(12) United States Patent
Brenneman et al.

(10) Patent No.: US 8,325,225 B2
(45) Date of Patent: Dec. 4, 2012

(54) METHOD AND APPARATUS FOR A WEB INSPECTION SYSTEM

(75) Inventors: Michael J. Brenneman, North Vancouver (CA); Richard T. Eagle, Port Coquitlam (CA); Kari K. Hilden, Vancouver (CA); Dave Narasimhan, Flemington, NJ (US)

(73) Assignee: PT Papertech, Inc, North Vancouver, BC (CA)

( * ) Notice: Subject to any disclaimer, the term of this patent is extended or adjusted under 35 U.S.C. 154(b) by 607 days.

(21) Appl. No.: 12/405,050

(22) Filed: Mar. 16, 2009

(65) Prior Publication Data

US 2010/0231704 A1 Sep. 16, 2010

(51) Int. Cl.
*H04N 9/47* (2006.01)
*H04N 7/18* (2006.01)

(52) U.S. Cl. ............................................. 348/88; 348/92
(58) Field of Classification Search ...................... 348/88, 348/92
See application file for complete search history.

(56) References Cited

U.S. PATENT DOCUMENTS

| | | | |
|---|---|---|---|
| 4,257,063 A | 3/1981 | Loughry et al. | |
| 4,814,869 A | 3/1989 | Oliver, Jr. | |
| 4,951,223 A | 8/1990 | Wales et al. | |
| 5,010,412 A | 4/1991 | Garriss | |
| 5,239,376 A | 8/1993 | Dittmann et al. | |
| 5,365,084 A * | 11/1994 | Cochran et al. | 250/559.02 |
| H1616 H * | 12/1996 | Wolfe | 348/88 |
| 5,668,611 A | 9/1997 | Ernstoff et al. | |
| 5,680,215 A | 10/1997 | Huber et al. | |
| 5,696,591 A * | 12/1997 | Bilhorn et al. | 356/429 |
| 5,835,163 A | 11/1998 | Liou et al. | |
| 6,236,429 B1 * | 5/2001 | Ho | 348/88 |
| 6,259,109 B1 * | 7/2001 | Dalmia et al. | 250/559.08 |
| 6,266,437 B1 * | 7/2001 | Eichel et al. | 382/149 |
| 6,528,954 B1 | 3/2003 | Lys et al. | |
| 6,624,597 B2 | 9/2003 | Dowling et al. | |
| 6,674,060 B2 | 1/2004 | Antila | |
| 6,750,466 B2 * | 6/2004 | Guha et al. | 250/559.46 |
| 7,259,522 B2 | 8/2007 | Toyota et al. | |
| 7,271,827 B2 | 9/2007 | Nister | |
| 7,393,119 B2 | 7/2008 | Lebens et al. | |
| 7,408,570 B2 * | 8/2008 | Guha et al. | 348/125 |
| 7,425,982 B2 * | 9/2008 | Joskin et al. | 348/142 |
| 7,773,226 B2 * | 8/2010 | Hofeldt et al. | 356/431 |
| 2005/0122422 A1 | 6/2005 | Kent et al. | |
| 2006/0058925 A1 | 3/2006 | Diederiks et al. | |
| 2006/0062424 A1 | 3/2006 | Diederiks et al. | |
| 2008/0101786 A1 | 5/2008 | Pozniansky et al. | |

* cited by examiner

*Primary Examiner* — Kristie Shingles
(74) *Attorney, Agent, or Firm* — Greenberg Traurig LLP; J. Rick Taché

(57) ABSTRACT

The present invention relates to a method and apparatus for a web inspection system. In one embodiment, the present invention is a web inspection system including a web moving unit moving a web of material, a camera positioned adjacent the web moving unit, the camera configured to be in an image capture state or a non-image-capture state, a first illumination system positioned adjacent the web moving unit, the first illumination system constantly illuminating the web of material, a second illumination system positioned adjacent the web moving unit, the second illumination system illuminating the web of material only when the camera is in the image capture state, and a control unit connected to the camera, the first illumination system, and the second illumination system.

19 Claims, 3 Drawing Sheets

METHOD AND APPARATUS FOR A WEB INSPECTION SYSTEM

BACKGROUND

1. Field

The present invention relates to a method and apparatus for a web inspection system.

2. Background

Current web inspection systems can utilize lights to illuminate a web in order to facilitate capturing an image of the web for later analysis. However, such systems tend to consume a large amount of energy and may be inefficient. Reducing an amount of lighting, however, can result in blurry images. Furthermore, the reduction in lighting can be dangerous as workers could be adversely affected by the light reduction.

Thus, there is a need for a web inspection system which operates in a more safe and efficient manner.

SUMMARY

In one embodiment, the present invention is a web inspection system including a web moving unit moving a web of material. A camera can positioned adjacent the web moving unit and configured to be in an image capture state or a non-image-capture state. Furthermore, the present invention can include a first illumination system and a second illumination system positioned adjacent the web moving unit. The first illumination system can constantly illuminate the web of material, while the second illumination system can illuminate the web of material only when the camera is in the image capture state. A control unit is also connected to the camera, the first illumination system, and the second illumination system.

In another embodiment, the present invention is a web inspection system including a web moving unit moving a web of material. A camera is positioned adjacent the web moving unit, and the camera can be configured to be in a first state or a second state. A first illumination system and a second illumination system can be positioned adjacent the web moving unit. The second illumination system illuminates the web of material only when the camera is in the first state.

In yet another embodiment, the present invention is a method for inspecting a web of material including the steps of moving the web of material and capturing an image of the web of material when a camera is in an image capture state. The present invention also includes constantly illuminating the web of material with a first illumination system, and illuminating the web of material with a second illumination system only when the camera is in the image capture state. In addition, a time period that a sensor in the camera is active is appropriately set to avoid blur in the images captured.

BRIEF DESCRIPTION OF THE DRAWINGS

The features, objects, and advantages of the present invention will become more apparent from the detailed description set forth below when taken in conjunction with the drawings, wherein.

DETAILED DESCRIPTION

Apparatus, systems and methods that implement the embodiments of the various features of the present invention will now be described with reference to the drawings. The drawings and the associated descriptions are provided to illustrate some embodiments of the present invention are and not intended to limit the scope of the present invention. Throughout the drawings, reference numbers are re-used to indicate correspondence between referenced elements.

Figure 1:
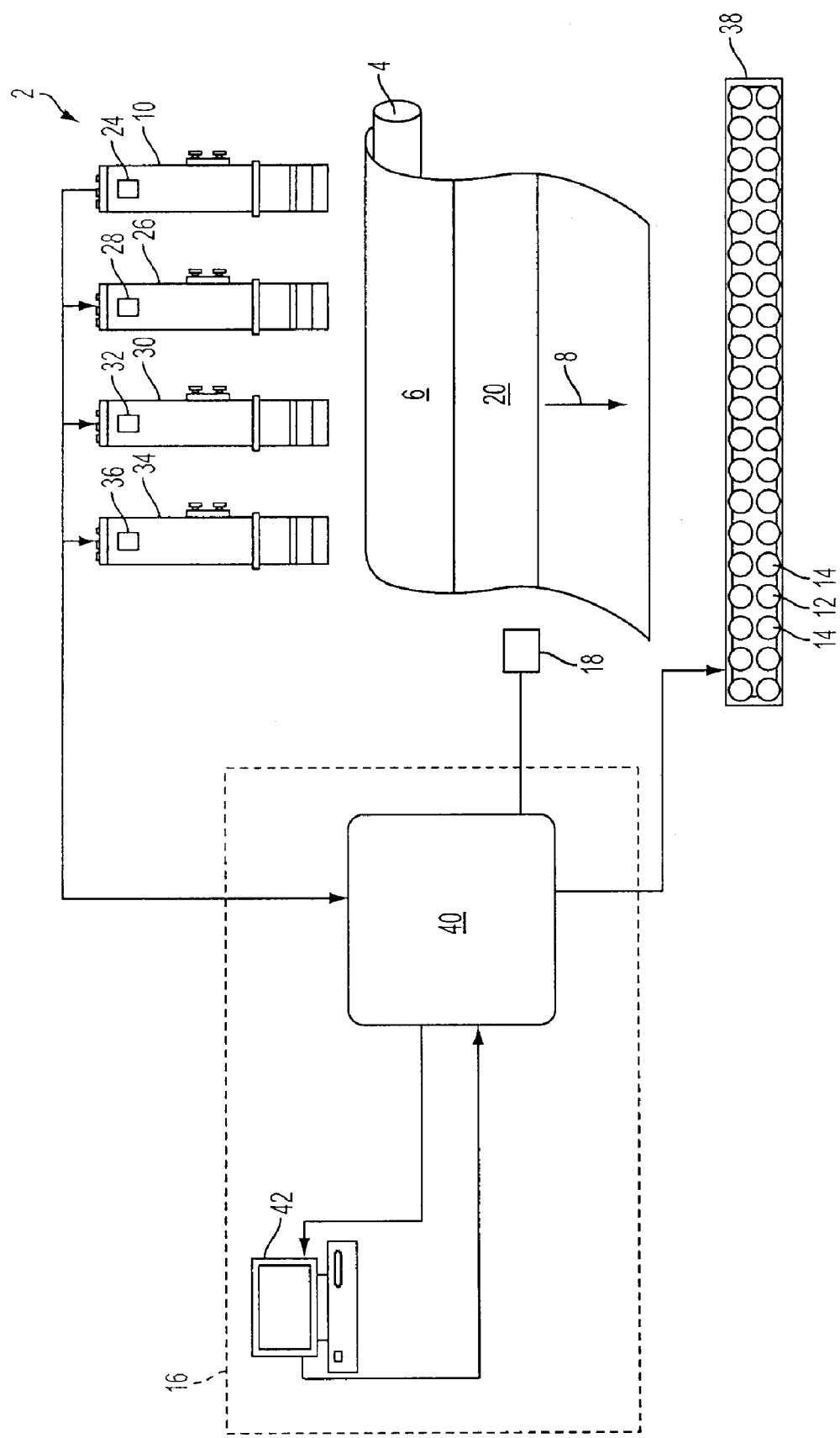
FIG. 1 is a schematic diagram of a web inspection system.

As seen in FIG. 1, a web inspection system 2 of the present invention includes a web moving unit 4, a camera 10, an illumination unit 38, a control unit 16, and a velocity detection unit 18.

Web moving unit 4 moves web 6 in a direction 8 with a velocity V. Web moving unit 4 can be, for example a conveyer belt or one or more rollers. However, web moving unit 4 can be any device which is capable of moving web 6 at a high velocity. It is contemplated that web moving unit 4 is capable of moving web 6 at a maximum velocity of $V_{max}$. Web 6 can be, for example, paper, fabric, food, or any other types of material having a web form.

Camera 10 is connected to control unit 16 for capturing one or more images of web 6 can/or select portions thereof. Camera 10 can be a video camera, a digital camera, or any other type of image or video capture device. Camera 10 could also be interlaced or progressive scan. Optionally web inspection system 2 can also include a camera 26, a camera 30, and a camera 34 with similar construction to camera 10. In one embodiment, camera 10, camera 26, camera 30, and camera 34 operate as equals and/or independently of each other. In another embodiment, one camera of camera 10, camera 26, camera 30, or camera 34 is a master camera, and the remaining cameras are slave cameras. In yet another embodiment, more than one camera of camera 10, camera 26, camera 30, or camera 34 is a master camera, and the remaining cameras are slave cameras. Camera 26, camera 30, and camera 34 can also have sensor 28, sensor 32, and sensor 36, respectively. The additional cameras could be controlled by control unit 16 and/or camera 10.

Figure 2:
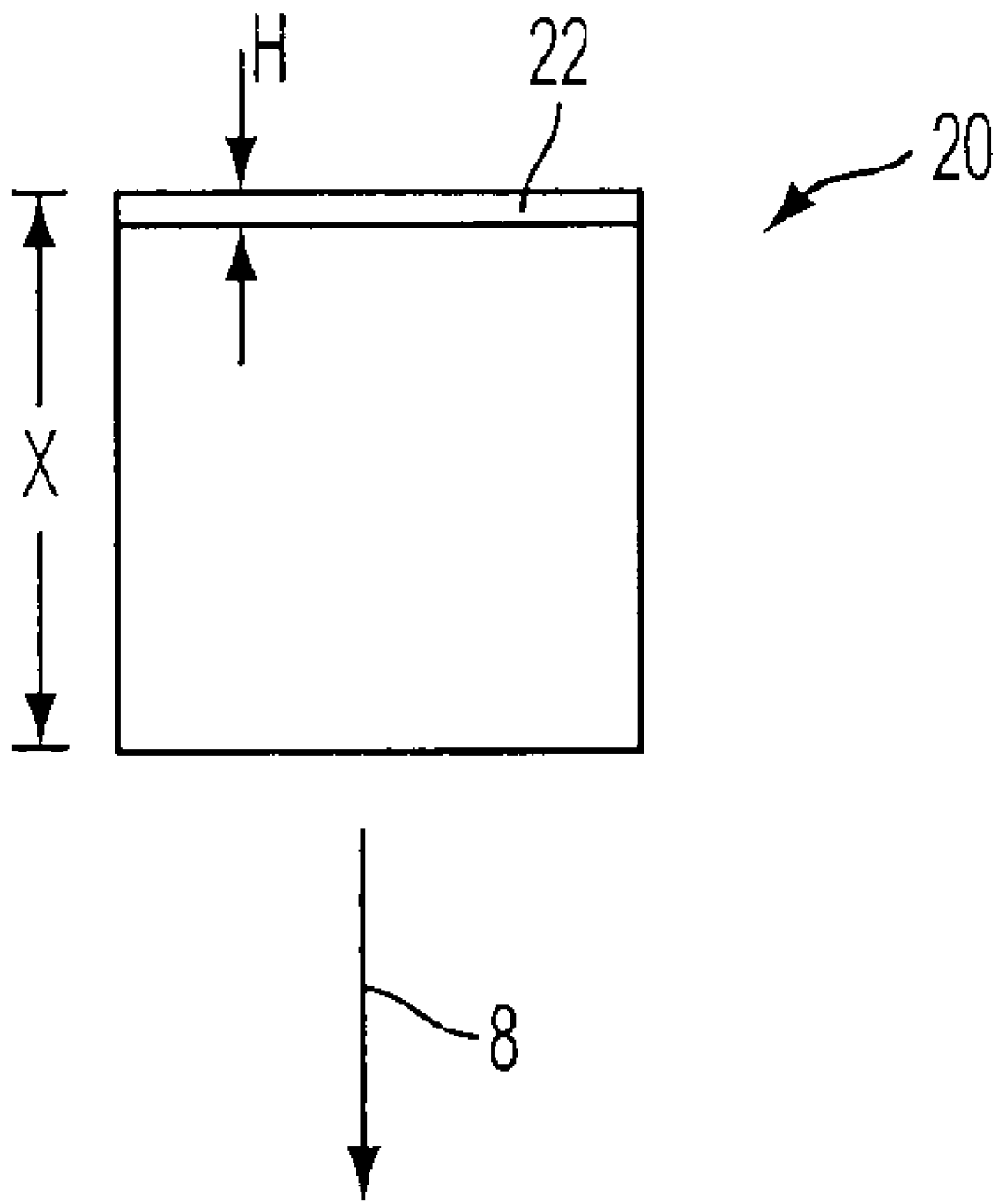
FIG. 2 is schematic diagram of a travelling web.

Camera 10 operates in an image capture state and in a non-image-capture state. During the image capture state, camera 10 is ready to capture an image of a portion 20 of web 6 as seen in FIG. 1 and FIG. 2. As seen in FIG. 2, portion 20 can have a height of X with multiple lines of pixels 22. Each line of pixel 22 can have a height H. Thus, if there are N lines of pixels in portion 20, each pixel can have a height H=X/N A time period T that camera 10 is in an image capture state can be dependent upon a velocity of web 6. In one embodiment, the time period T that camera 10 is in the image capture state is equal to or less than $H/V_{max}$. In another embodiment, velocity detection unit 18 is connected to control unit 16 and detects a velocity $V_{actual}$ of web 6. The time period T that camera 10 is in the image capture state is equal to or less than $H/V_{actual}$.

It is also contemplated that camera 10 can have a sensor 24. In one embodiment sensor 24 is active when camera 10 is in the image capture state. Sensor 24 can be active for all or only a part of time period T, and when sensor 24 is active, the image can be captured. During the non-image-capture state, sensor 24 can be inactive.

Illumination unit 38 includes first illumination system 12 and second illumination system 14 and is connected to control unit 16. First illumination system 12 and second illumination system 14 can illuminate portion 20 of web 6. Illumination unit 38 can be, for example, a LED light bar, a HID light bar, or any other type of illumination device capable of illuminating an object. First illumination system 12 and second illumination system 14 can be, for example, light emitting diodes (LED) lights, high intensity discharge (HID)

lights, lamps, strobe lights, or any other type of lighting device capable of illuminating an object.

One of first illumination system 12 or second illumination system 14 can be constantly illuminating portion 20 while the other of first illumination system 12 or second illumination system 14 can alternate between illumination portion 20 and not illumination portion 20. For example, first illumination system 12 can be constantly illuminating portion 20 while second illumination system 14 alternates between illuminating portion 20 and not illuminating portion 20 such as by flashing. In one embodiment, second illumination system 14 illuminates portion 20 only when the camera is an image capture state. In another embodiment, second illumination system 14 illuminates portion 20 only when sensor 24 is active.

It is contemplated that through constant illumination of portion 20 with first illumination system 12 and through alternating illumination of portion 20 with second illumination system 14, users around web 6 could feel less discomfort. That is, since first illumination system 12 is constantly on, the users may have a reduced awareness of second illumination system 14 alternating its illumination of portion 20. This can be safer for the users because there could be a lower risk of the user being affected by the flashing of second illumination system 14. That is, there could be a reduced likelihood that the user could be distracted by the flashing of second illumination system 14. In addition, since the user is less likely to notice the flashing of second illumination system 14, there could also be a reduced risk of medical problems such as injury to the eye due to the sudden increase in light intensity, or even epileptic seizures.

Furthermore, since second illumination system 14 alternates between illuminating and not illuminating portion 20, it is contemplated that second illumination system 14 could use less energy than if second illumination system 14 was constantly on. Thus, second illumination portion could have a duty cycle C=A/P. Where A is the time period that second illumination portion is active and illuminating portion 20 and P is the total time period where camera 10 is in the image capture state and the non-image-capture state. When second illumination portion 14 illuminates portion 20 when camera 10 is the image capture state, A could equal T. Thus, the duty cycle D of second illumination system 14 could be equal to T/P. In addition, since second illumination system 14 is not constantly on, its operational life could be extended due to a reduction in wear and tear.

Since second illumination system 14 could have a reduced duty cycle in the present invention, an amount of heat generated by second illumination system 14 could also be reduced. With a reduced amount of heat generated by second illumination system 14, a reduced amount of power could be expended to cool second illumination system 14 and/or an area surrounding second illumination system 14. This can further reduce an operational cost of web inspection system 2.

First illumination system 12 could operate at a brightness value $B_1$ while second illumination system 14 could operate at a brightness value $B_2$. In one embodiment, $B_2$ is greater than $B_1$. Beneficially by having $B_2$ be greater than $B_1$, it is contemplated that the pupils in the eye could be increased to reduce the observable effects of the flashing of second illumination system 14. However, in another embodiment, $B_2$ could also be equal to or less than $B_1$.

Although first illumination system 12 and second illumination system 14 are part of illumination unit 38, they can exist independently of illumination unit 38. Also, first illumination system 12 and second illumination system 14 can be located in any location such that first illumination system 12 and second illumination system 14 can illuminate portion 20. Furthermore, there can be any number of first illumination system 12 and second illumination system 14 and the ratio of first illumination system 12 to second illumination system 14 can be any appropriate ratio. Thus, there can be more of first illumination system 12 than second illumination system 14, a same amount of first illumination system as second illumination system 14, or less of first illumination system 12 than second illumination system 14.

Control unit 16 is connected to camera 10, first illumination system 12, second illumination system 14, and velocity detection unit 18 either through wires or wirelessly such as with RF waves, Bluetooth, the Internet, or any other suitable connections. Optionally, control unit 16 can also be connected to camera 26, camera 30, and/or camera 34. Control unit 16 can include, for example, a processor (not shown), a computer 42, and/or a driver board 40.

Computer 42 can send control parameter signals to driver board 40 which can control camera 10, camera 26, camera 30, camera 34, and/or illumination unit 38. Driver board 40 can also send video signals to computer 42. In one embodiment, computer 42 receives information regarding the resolution of camera 10, camera 26, camera 30, and/or camera 34 and can set the shutter speed of camera 10, camera 26, camera 30, and/or camera 34. Computer 42 can also calculate the shutter speed such that blur is reduced or eliminated in any images captured by camera 10, camera 26, camera 30, and/or camera 34. In addition control unit 16 can set an aperture and gain of camera 10, camera 26, camera 30, and/or camera 34 to an appropriate f-number such that there is an appropriate depth of field and the gain is set to generate a clear, non-grainy image at the shutter speed which reduces or eliminates blur.

Control unit 16 can also control the operations of first illumination system 12, second illumination system 14, and velocity detection unit 18 and can send the appropriate values and signals to each of the components. For example, control unit 16 can control the first illumination system 12 and the second illumination system 14 using a signal. Driver board 40 can send and receive video synchronization signals and/or power to camera 10, camera 26, camera 30, and camera 34. In addition driver board 40 can send or receive control signals and/or power to illumination unit 38 and its components such as first illumination system 12 and second illumination system 14. In addition, although not shown, control unit 16 could also be connected to web moving unit 4.

Figure 3:
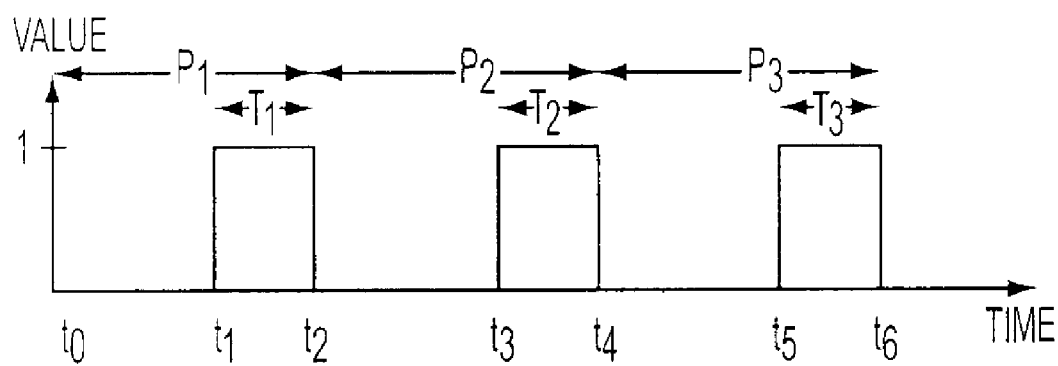
FIG. 3 is a timing graph for a camera.

In operation, as seen in FIG. 3, control unit 16 sets camera 10 in an image capture state during time periods $T_1$, $T_2$, and $T_3$ in time periods $P_1$, $P_2$, and $P_3$. Time period $T_1$ spans from time $t_1$ to time $t_2$, time period $T_2$ spans from time $t_3$ to time $t_4$, and time period $T_3$ spans from time $t_5$ to time $t_6$. Time period $P_1$ spans from time $t_0$ to time $t_2$, time period $P_2$ spans from time $t_2$ to time $t_4$, and time period $P_3$ spans from time $t_4$ to time $t_6$. Time period, $T_n$ with n=1, 2, 3, etc. could be based on a velocity of web 6 and governed by the equation H/V where V could be $V_{max}$ or $V_{actual}$. By setting the time period $T_n$ equal to H/V, it is contemplated that an amount of blur in the image captured by camera 10 could be reduced or eliminated.

Although $T_1$, $T_2$, and $T_3$ appear to have equal lengths of time periods in FIG. 3, it is contemplated that they could also have different lengths of time periods. In one embodiment, $V_{actual}$ is periodically updated by velocity detection unit 18. Control unit 16 could set camera 10 in a non-image-capture state between time $t_0$ to $t_1$, $t_2$ to $t_3$, and $t_4$ to $t_5$.

Figure 4:
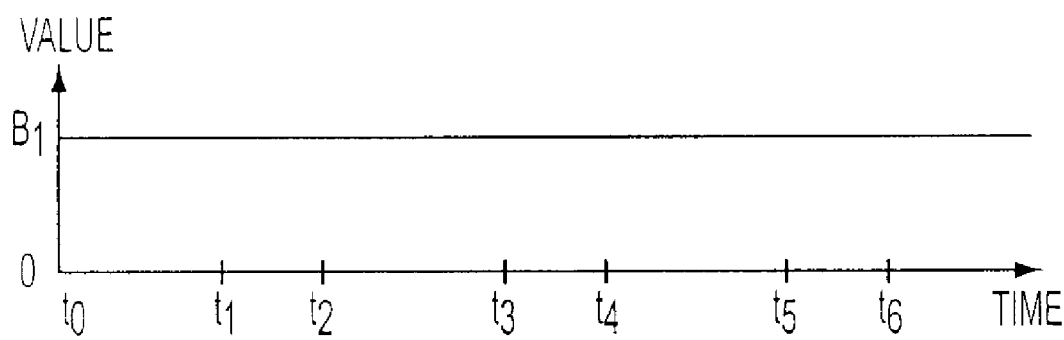
FIG. 4 is a timing graph for an illumination system.
Figure 5:
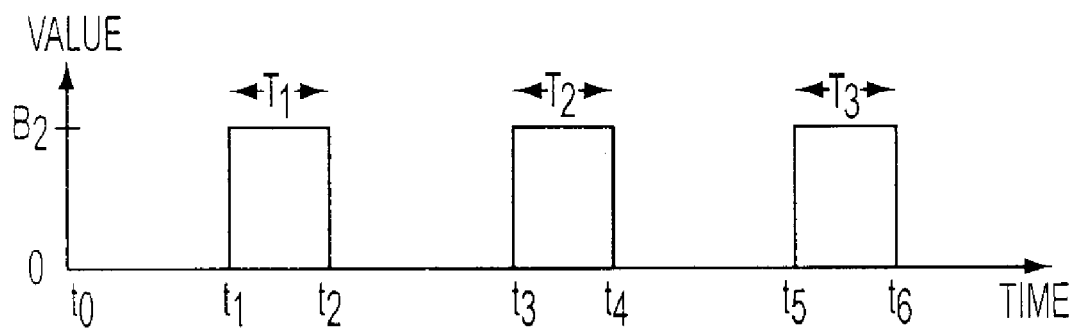
FIG. 5 is a timing graph for an illumination system.

As seen in FIG. 4, control unit 16 sets first illumination system 12 to constantly illuminate portion 20 with a brightness value of $B_1$. As seen in FIG. 5, control unit 16 sets second illumination system 14 to illuminate portion 20 with a brightness value of $B_2$ when camera 10 is in an active image capture state and to not illuminate portion 20 when camera 10 is in a non-image-capture state. In one embodiment the values of $B_1$ and $B_2$ could vary according to an available amount of ambient lighting.

The previous description of the disclosed examples is provided to enable any person of ordinary skill in the art to make or use the disclosed methods and apparatus. Various modifications to these examples will be readily apparent to those skilled in the art, and the principles defined herein may be applied to other examples without departing from the spirit or scope of the disclosed method and apparatus. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. A web inspection system comprising:
    a web moving unit moving a web of material;
    a camera positioned adjacent the web moving unit, the camera configured to be in an image capture state or a non-image-capture state, wherein the camera includes a sensor which is active during the image capture state;
    a first illumination system positioned adjacent the web moving unit, the first illumination system illuminating the web of material;
    a second illumination system positioned adjacent the web moving unit;
    a control unit connected to the camera, the first illumination system, and the second illumination system, wherein the control unit is configured to control the second illumination system such that the second illumination system illuminates the web of material when the camera is in the image capture state and does not illuminate the web of material when the camera is in the non-image-capture state; and
    a velocity detection unit connected to the control unit for obtaining an actual velocity of the web of material, wherein the time period the sensor is active is related to the actual velocity of the web of material.

2. The web inspection system of claim 1, wherein a time period that the sensor is active is less than $H/V_{max}$, where H is a height of a single line of pixels of an image captured by the camera and $V_{max}$ is a maximum velocity of the web of material.

3. The web inspection system of claim 1, wherein the control unit sets the time period that the sensor is active.

4. The web inspection system of claim 1, wherein the time period the sensor is active is less than $H/V_{actual}$, where H is a height of a single line of pixels of an image captured by the camera and $V_{actual}$ is the actual velocity of the web of material.

5. The web inspection system of claim 4, wherein the first illumination system and the second illumination system illuminate illuminates a same area of the web of material.

6. The web inspection system of claim 5, wherein the first illumination system illuminates the web of material at a first illumination value and the second illumination system illuminates the web of material at a second illumination value, the first illumination value and the second illumination value being controlled by the control unit such that the second illumination value is greater than the first illumination value.

7. A web inspection system comprising:
    a web moving unit moving a web of material;
    a camera positioned adjacent the web moving unit, the camera configured to be in a first state or a second state, wherein the camera includes a sensor which is active during the first state;
    a first illumination system positioned adjacent the web moving unit, the first illumination system illuminating the web of material; and
    a second illumination system positioned adjacent the web moving unit, wherein the second illumination system illuminates the web of material when the camera is in the first state and does not illuminate the web of material when the camera is in the second state; and
    a velocity detection unit for obtaining an actual velocity of the web of material, and wherein the time period the sensor is active is related to the actual velocity.

8. The web inspection system of claim 7, further comprising a control unit connected to the camera, the first illumination system, and the second illumination system.

9. The web inspection system of claim 7, wherein the first state is an image capture state, and the second state is a non-image-capture state.

10. The web inspection system of claim 8, wherein the first illumination system is constantly illuminating the web of material.

11. The web inspection system of claim 10, wherein a time period the sensor is active is less than $H/V_{max}$, where H is a height of a single line of pixels of an image captured by the camera and $V_{max}$ is a maximum velocity of the web of material.

12. The web inspection system of claim 11, wherein the control unit sets the time period the sensor is active.

13. The web inspection system of claim 12, wherein the time period the sensor is active is less than $H/V_{actual}$, where $V_{actual}$ is the actual velocity of the web of material.

14. The web inspection system of claim 13, wherein the first illumination system illuminates the web of material at a first illumination value and the second illumination system illuminates the web of material at a second illumination value, the first illumination value and the second illumination value being controlled by the control unit.

15. The web inspection system of claim 14, wherein the second illumination value is greater than the first illumination value.

16. The web inspection system of claim 15, wherein the first illumination system and the second illumination system illuminate a same area of the web of material.

17. A method for inspecting a web of material, the method comprising:
    moving the web of material;
    capturing an image of the web of material when a camera is in an image capture state;
    illuminating the web of material with a first illumination system;
    illuminating the web of material with a second illumination system when the camera is in the image capture state and not illuminating the web of material when the camera is in a non-image-capture state;
    obtaining an actual velocity of the web of material; and
    setting a time period that a sensor in the camera is active in relation to the actual velocity.

18. The web inspection method of claim 17, further comprising:
    setting the time period the sensor is active to be less than $H/V_{actual}$, where H is a height of a single line of pixels of the image captured by the camera and $V_{actual}$ is the actual velocity of the web of material.

19. The web inspection method of claim 18, further comprising:
- illuminating a same area of the web of material with the first illumination system and the second illumination system;
- illuminating the web of material at a first illumination value with the first illumination system; and
- illuminating the web of material at a second illumination value with the second illumination system, such that the second illumination value is greater than the first illumination value.

* * * * *